(12) United States Patent
Cha et al.

(10) Patent No.: US 8,618,294 B2
(45) Date of Patent: Dec. 31, 2013

(54) DYE FOR DYE-SENSITIZED SOLAR CELLS, METHOD OF PREPARING THE SAME, AND SOLAR CELL INCLUDING THE DYE

(75) Inventors: Si-Young Cha, Yongin-si (KR); Ji-Won Lee, Yongin-si (KR); Moon-Sung Kang, Yongin-si (KR); Byong-Cheol Shin, Yongin-si (KR); Do-Young Park, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 223 days.

(21) Appl. No.: 12/964,590

(22) Filed: Dec. 9, 2010

(65) Prior Publication Data

US 2012/0006410 A1    Jan. 12, 2012

(30) Foreign Application Priority Data

Jul. 9, 2010   (KR) .................. 10-2010-0066410

(51) Int. Cl.
*C07F 15/00*    (2006.01)
*H01L 31/042*   (2006.01)

(52) U.S. Cl.
USPC ............................... 546/2; 136/263; 136/252

(58) Field of Classification Search
USPC ...................... 546/2; 136/252, 263
See application file for complete search history.

(56) References Cited

U.S. PATENT DOCUMENTS

| | | | |
|---|---|---|---|
| 2008/0015356 A1 | 1/2008 | Kakuta et al. | |
| 2009/0000658 A1 | 1/2009 | Zakeeruddin et al. | |
| 2010/0084018 A1 | 4/2010 | Chen et al. | |

FOREIGN PATENT DOCUMENTS

| | | |
|---|---|---|
| EP | 1 052 661 A2 | 11/2000 |
| EP | 2 061 102 A1 | 5/2009 |
| EP | 2 112 701 A1 | 10/2009 |
| JP | 2000-323191 | 11/2000 |
| JP | 2001-291534 | 10/2001 |
| JP | 2005-330469 | 12/2005 |
| JP | 2006-143646 | 6/2006 |
| JP | 2007-332098 | 12/2007 |
| KR | 10-2007-0085221 A | 8/2007 |
| KR | 10-2008-0049197 A | 6/2008 |
| WO | WO 2006/038587 A1 | 4/2006 |

OTHER PUBLICATIONS

Nazeeruddin, M., et al., *Engineering of Efficient Panchromatic Sensitizers for Nanocrystalline TiO₂-Based Solar Cells*, Journal of American Chemical Society, (2001), vol. 123, pp. 1613-1624.
European Search Report daed Dec. 20, 2011, for corresponding European Patent application 11156623.8, noting listed references in this IDS, 8 pages.
KIPO Office action dated Jun. 20, 2012 for Application No. 10-2010-0066410 (4 pages).
KIPO Notice of Allowance dated Jul. 15, 2013, for Korean priority Patent application 10-2010-0066410, (6 pages).
Patent Abstracts of Japan, and English machine translation of Japanese Publication 2001-291534 dated Oct. 19, 2001, listed above, (194 pages).

*Primary Examiner* — Charanjit Aulakh
(74) *Attorney, Agent, or Firm* — Christie, Parker & Hale, LLP

(57) ABSTRACT

A dye for dye-sensitized solar cells includes an organometallic complex represented by $M(L)_pX_2:(Z)_q$. In the organometallic complex, M is a Group 8 through Group 10 metallic element, L is a bidentate ligand, X is a co-ligand, and Z is a counter-ion. The ratio of the bidentate ligand (L) to the counter-ion (Z) is about 1.1 to about 1.4. A method of preparing an exemplary dye includes mixing the organometallic complex with tetrabutylammonium thiocyanate and tetrabutylammonium hydroxide to prepare a solution, and purifying the solution at a pH of about 3.8 to about 4.1. A dye-sensitized solar cell includes a first electrode with a light absorbing layer, a second electrode and an electrolyte between the first and second electrodes. The light absorbing layer includes the dye.

16 Claims, 8 Drawing Sheets

DYE FOR DYE-SENSITIZED SOLAR CELLS, METHOD OF PREPARING THE SAME, AND SOLAR CELL INCLUDING THE DYE

RELATED APPLICATIONS

This application claims priority to and the benefit of Korean Patent Application No. 10-2010-0066410, filed on Jul. 9, 2010 in the Korean Intellectual Property Office, the entire content of which is incorporated herein by reference.

BACKGROUND

1. Field

One or more embodiments of the present invention relate to dyes for dye-sensitized solar cells, methods of preparing the same, and solar cells including the dyes.

2. Description of the Related Art

In an effort to address current energy problems, much research is being conducted into alternatives to existing fossil fuel. For example, a wide range of research into natural energy sources, such as wind power, atomic power, and solar power, is being conducted in an effort to replace petroleum resources, which will be depleted within a few decades. Among these energy sources, solar cells using solar energy (unlike other energy sources) provide unlimited energy and are environmentally friendly. A selenium (Se) solar cell was developed in 1983, and thereafter, silicon solar cells have been receiving attention.

However, the manufacturing costs associated with such silicon solar cells are very high, and thus, it is difficult to make them commercially viable, and battery efficiency is difficult to achieve. In order to address these problems, many efforts have been made to develop inexpensive dye-sensitized solar cells.

Unlike silicon solar cells, dye-sensitized solar cells are photoelectric, chemical solar cells mainly composed of a photosensitive dye molecule that absorbs visible light and generates electron-hole pairs, and a transition metal oxide that delivers generated electrons. An example of a known dye-sensitized solar cell is the solar cell developed by Gratzel et al. of Switzerland in 1991. Dye-sensitized solar cells have lower manufacturing costs per electric power unit than conventional silicon solar cells. Due to such low manufacturing costs, dye-sensitized solar cells are considered an alternative to conventional solar cells.

A conventional structure of such a dye-sensitized solar cell includes a conductive transparent substrate, a light absorbing layer, an electrolyte layer, and an opposite electrode, where the light absorbing layer includes semiconducting microparticles and a dye. An operational method of the conventional dye-sensitized solar cell will now be described briefly. When solar light is absorbed by dye molecules, the dye molecules transition from a ground state to an excited state and generate electron-hole pairs. Excited electrons migrate to a conduction band at an interface between titanium oxide particles and the dye molecules. Injected electrons are delivered to the conductive transparent substrate via an interface between the conductive transparent substrate and the titanium oxide particles and move to an opposite electrode via an external circuit. Meanwhile, the dye molecules that are oxidized by the electron transition are reduced by an ion of a redox couple in the electrolyte layer, and the oxidized ion and electrons arriving at the interface between the opposite electrode and the electrolyte layer participate in a reduction reaction to achieve charge neutrality.

In the operational method described above, the first operation is to generate photo charges from photo energy, and to do this, the dye molecules are excited by absorbing light that is transmitted through the conductive transparent substrate. The dye molecules may include an organometallic complex.

Although such dye molecules have high proton yields, their efficiency in a solar cell is insufficient. Accordingly, there is a need to develop dyes having improved performance.

SUMMARY

According to one or more embodiments of the present invention, a dye for a dye-sensitized solar cell includes an organometallic complex having a bidentate ligand and a counter-ion in a different ratio from that of conventional organometallic complexes.

In one or more embodiments of the present invention, a method of manufacturing the dye for the dye-sensitized solar cell is provided.

According to one or more embodiments of the present invention, a solar cell includes the dye for the dye-sensitized solar cell.

Additional aspects will be set forth in part in the description which follows and, in part, will be apparent from the description, or may be learned by practice of the described embodiments.

According to one or more embodiments of the present invention, a dye for a dye-sensitized solar cell includes an organometallic complex represented by Formula 1:

$$M(L)_p X_2 : (Z)_q \quad \text{Formula 1}$$

In Formula 1, M is an element selected from Group 8 through 10 metallic elements. X is a co-ligand selected from —CN, —OH, —I, —Cl, —NCO, —NCS, and —NCSe. L is a bidentate ligand represented by Formula 2 below:

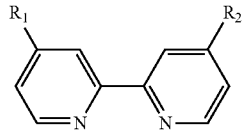

Formula 2

In Formula 1, Z is a counter-ion represented by Formula 3 below:

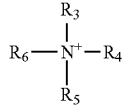

Formula 3

In Formulae 2 and 3, each of $R_1$ and $R_2$ is independently selected from COOH, $PO_3H_2$, $PO_4H_2$, $SO_3H_2$, $SO_4H_2$, and CONHOH, and any one of $R_1$ and $R_2$ may be deprotonized. Each of $R_3$ through $R_6$ is independently selected from substituted or unsubstituted $C_{1-20}$ alkyl groups, substituted or unsubstituted $C_{1-20}$ alkoxy groups, substituted or unsubstituted $C_{2-20}$ alkenyl groups, substituted or unsubstituted $C_{2-20}$ alkynyl groups, substituted or unsubstituted $C_{6-30}$ aryl groups, substituted or unsubstituted $C_{6-30}$ aryloxy groups, and substituted or unsubstituted $C_{2-30}$ heteroaryl groups.

In Formula 1, the mole ratio of L to Z (i.e., the ratio of p/q) is in a range of about 1.1 to about 1.4.

In some embodiments, in Formula 1, M is ruthenium (Ru).

In some embodiments, in Formula 1, X is —NCS.

In some embodiments, in Formula 1, L is represented by Formula 4 below:

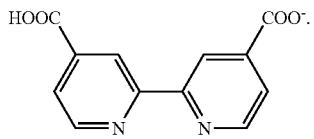

Formula 4

In some embodiments, in Formula 1, Z is represented by Formula 5 below:

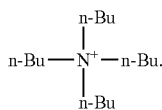

Formula 5

The dye may include about 70 to about 99 wt % of an organometallic complex represented by Formula 6 below:

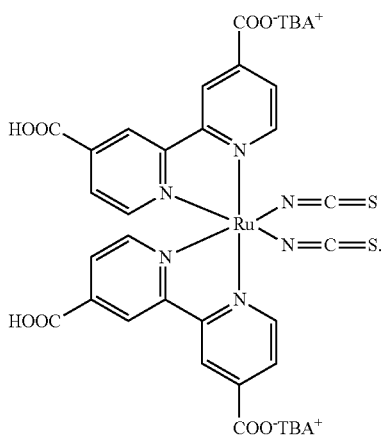

Formula 6

According to one or more embodiments of the present invention, a method of preparing the dye described above includes: preparing an organometallic complex represented by Formula 7 below, mixing 100 parts by weight of the organometallic complex, about 80 to about 150 parts by weight of tetrabutylammonium thiocyanate, and about 20 to about 80 parts by weight of tetrabutylammonium hydroxide to prepare a solution, and purifying the solution at a pH of about 3.8 to about 4.1.

$$ML_2X_2{:}Z_2 \qquad \text{Formula 7}$$

In Formula 7, M, X, L, and Z are as described above.

According to one or more embodiments of the present invention, a dye-sensitized solar cell includes: a first electrode including a conductive transparent substrate; a light absorbing layer formed on a surface of the first electrode; a second electrode disposed facing the surface of the first electrode on which the light absorbing layer is formed; and an electrolyte between the first electrode and the second electrode. The light absorbing layer includes micro-semiconducting particles and the dye described above.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
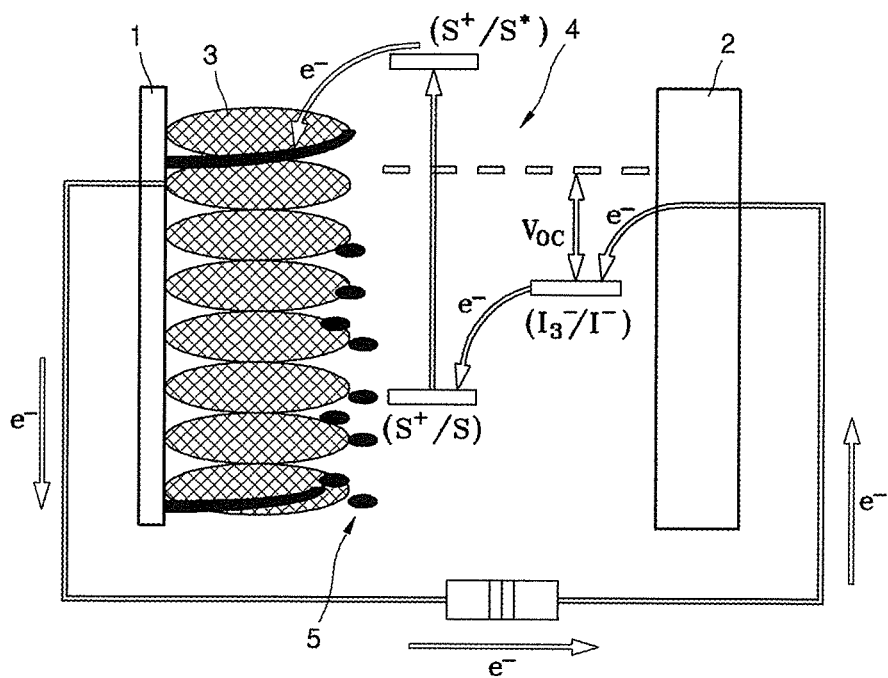
FIG. 1 is a schematic view illustrating the operational principle of a dye-sensitized solar cell.

Some exemplary embodiments of the present invention will now be described with reference to the accompanying drawings. Like reference numerals refer to the like elements throughout. The described embodiments may take different forms and should not be construed as being limited to the descriptions set forth herein. Accordingly, the described embodiments are merely exemplary and refer to the figures to explain certain aspects of the present invention.

Hereinafter, one or more embodiments of a dye for a dye-sensitized solar cell, a method of preparing the same, and a solar cell including the same will be described.

A dye for a dye-sensitized solar cell according to an embodiment of the present invention includes an organometallic complex represented by Formula 1:

$$M(L)_p X_2{:}(Z)_q \qquad \text{Formula 1}$$

In Formula 1, M is an element selected from Group 8 through 10 metallic elements. X is a co-ligand selected from —CN, —OH, —I, —Cl, —NCO, —NCS, and —NCSe. L is a bidentate ligand represented by Formula 2 below. Z is a counter-ion represented by Formula 3 below. A mole ratio of L to Z (i.e., the mole ratio of p/q) is in the range of about 1.1 to about 1.4:

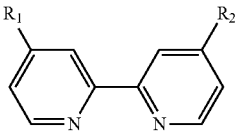

Formula 2

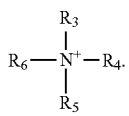

Formula 3

In Formula 2, each of $R_1$ and $R_2$ is independently selected from COOH, $PO_3H_2$, $PO_4H_2$, $SO_3H_2$, $SO_4H_2$, and CONHOH. Any one of $R_1$ and $R_2$ may be deprotonized. In Formula 3, each of $R_3$ through $R_6$ is independently selected from substituted or unsubstituted $C_{1-20}$ alkyl groups, substituted or unsubstituted $C_{1-20}$ alkoxy groups, substituted or unsubstituted $C_{2-20}$ alkenyl groups, substituted or unsubstituted $C_{2-20}$ alkynyl groups, substituted or unsubstituted $C_{6-30}$ aryl groups, substituted or unsubstituted $C_{6-30}$ aryloxy groups, and substituted or unsubstituted $C_{2-30}$ heteroaryl groups.

FIG. 1 is a schematic view of the operational principle of a dye-sensitized solar cell. Referring to FIG. 1, the dye-sensitized solar cell operates as follows: when solar light is absorbed by dye molecules 5, the dye molecules 5 transition from a ground state to an excited state and generate electron-hole pairs. Excited electrons migrate to a conduction band at an interface between a porous layer 3 and the dye molecules 5 and the electrons are delivered to a first electrode 1 via an interface between the first electrode 1 and the porous layer 3 and move to a second electrode via an external circuit. Meanwhile, the dye molecules 5 that are oxidized by the electron transition are reduced by an iodine ion (I⁻) of a redox couple in an electrolytic solution 4, and the oxidized trivalent iodine ion (I₃⁻) and electrons arriving at an interface between the second electrode 2 and the electrolytic solution 4 participate in a reduction reaction to achieve charge neutrality. As described above, and unlike conventional p-n junction type silicon based solar cells, the dye-sensitized solar cell operates electrochemically by interface reactions.

The organometallic complex represented by Formula 1 has the basic structure of Gratzel's dye used in a dye-sensitized solar cell and includes two bidentate ligands (L) and two co-ligands (X). In the organometallic complex represented by Formula 1, the mole ratio of the bidentate ligand to the counter-ion is controlled to be in a certain range.

In Formula 1, M is an element selected from Group 8 through 10 metallic elements. For example, M is selected from ruthenium (Ru), osmium (Os), iron (Fe), and rhenium (Rh). For example, M may be Ru.

In Formula 1, L is a bidentate ligand that is coordinately bonded with M, and may be represented by Formula 2 below:

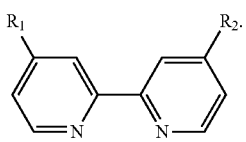

Formula 2

In Formula 2, each of $R_1$ and $R_2$ is independently selected from COOH, $PO_3H_2$, $PO_4H_2$, $SO_3H_2$, $SO_4H_2$, and CONHOH. Any one of $R_1$ and $R_2$ may be deprotonized.

In the organometallic complex of Formula 1, the element selected from Group 8 through 10 metallic elements is located at the center of the organometallic complex. Two bidentate ligands (L), each represented by Formula 2, are linked to the element, and two co-ligands (X) are also linked to the element. In the organometallic complex described above, the bidentate ligand (L) represented by Formula 2 constitutes a back bone. Accordingly, the characteristics of the organometallic complex are mostly dependent upon the structure of the bidentate ligand (L) represented by Formula 2.

L has —N, and thus, non-shared electron pairs of the nitrogen atom are strongly bonded to M. Organometallic complexes having such a strong coordination bond are well adsorbed to surfaces of micro-semiconducting particles in a light absorbing layer. Accordingly, when the organometallic complex is used as a dye of a solar cell, electrons generated by the dye molecules move easily to the micro-semiconducting particles and thus the photo conversion efficiency of the solar cell may be improved. That is, an organometallic complex including the bidentate ligand (L) represented by Formula 2 has enhanced adsorption ability at the interfaces between the dye molecules and the micro semiconducting particles. Thus, the interface resistance is reduced and electrons move smoothly, and the smooth movement of the electrons leads to a high photo conversion efficiency.

Since $R_1$ and $R_2$ (which are terminal groups of the bidentate ligand (L)) greatly affect the characteristics of the bidentate ligand (L) itself, $R_1$ and $R_2$ may also greatly affect the adsorption capability of the organometallic complex represented by Formula 1. $R_1$ and $R_2$ may be highly reactive acids. For example, $R_1$ and $R_2$ may be selected from COOH, $PO_3H_2$, $PO_4H_2$, $SO_3H_2$, $SO_4H_2$, and CONHOH.

For example, the bidentate ligand (L) may be represented by Formula 4, in which a bipyridine backbone containing nitrogen has a non-shared electron pair and is linked to —COOH terminal groups. In this regard, one of the COOH terminal groups may be deprotonized by removing one hydrogen atom therefrom.

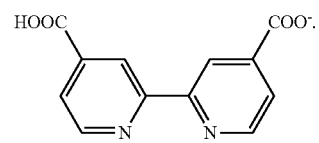

Formula 4

Since the bidentate ligand (L) represented by Formula 4 includes a non-shared electron pair and —COOH, the affinity of the organometallic complex with respect to the micro-semiconducting particles in the light absorbing layer may be improved. Thus, at the interfaces between the organometallic complex and the micro-semiconducting particles, electrons may migrate smoothly.

In Formula 1, Z is a counter-ion of the bidentate ligand (L), and may be represented by Formula 3.

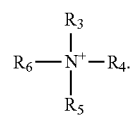

Formula 3

In Formula 3, each of $R_3$ through $R_6$ may be independently selected from substituted or unsubstituted $C_{1-20}$ alkyl groups, substituted or unsubstituted $C_{1-20}$ alkoxy groups, substituted or unsubstituted $C_{2-20}$ alkenyl groups, substituted or unsubstituted $C_{2-20}$ alkynyl groups, substituted or unsubstituted $C_{6-30}$ aryl groups, substituted or unsubstituted $C_{6-30}$ aryloxy groups, and substituted or unsubstituted $C_{2-30}$ heteroaryl groups.

Z is a counter-ion corresponding to one of the terminal groups of the bidentate ligand (L) (that is, any one of $R_1$ and $R_2$ is deprotonized by the removal of a hydrogen atom). The counter-ion (Z) is a monovalent cation containing an N atom and four functional groups linked to bonding sites of the N atom. The functional groups linked to the N atom located at the center of the counter-ion (Z) may be selected from substituted or unsubstituted $C_{1-20}$ alkyl groups, substituted or unsubstituted $C_{1-20}$ alkoxy groups, substituted or unsubstituted $C_{2-20}$ alkenyl groups, substituted or unsubstituted $C_{2-20}$ alkynyl groups, substituted or unsubstituted $C_{6-30}$ aryl groups, substituted or unsubstituted $C_{6-30}$ aryloxy groups, and substituted or unsubstituted $C_{2-30}$ heteroaryl groups.

For example, Z may be a tetrabutylammonium ion (TBA⁺) in which an N atom is linked to four n-butyl groups, and the tetrabutylammonium ion (TBA⁺) may be represented by Formula 5.

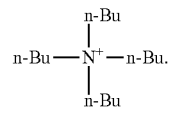

Formula 5

In Formula 1, X may be a co-ligand for charge-neutralizing the organometallic complex. For example, X may be selected from —CN, —OH, —I, —Cl, —NCO, —NCS, or —NCSe, taking into consideration the electrochemical characteristics. For example, X may be —NCS.

In Formula 1, the mole ratio of L to Z (i.e., the mole ratio of p to q) may be in the range of about 1.1 to about 1.4. The mole ratio of L to Z is the mole ratio of the bidentate ligand represented by Formula 2 to the counter-ion represented by Formula 3. Ideally, one bidentate ligand is paired with one counter-ion. This is because the bidentate ligand is a monovalent anion formed due to the removal of hydrogen from one terminal group, and the counter-ion is a monovalent cation formed due to the absence of a non-shared electron pair of the nitrogen. Accordingly, the ideal mole ratio of L to Z is 1. However, in practice, when the mole ratio of L to Z (p/q) is 1 or more, high conversion efficiency may be obtained due to the adsorption characteristics of the dye. That is, since L contains, for example, an anchoring group (—COO$^-$H$^+$) that affects adsorption characteristics of the dye with respect to a porous titanium oxide surface, a higher ratio of p to q may lead to more adsorption of the dye with respect to an electrode.

Meanwhile, if the mole ratio of L to Z (p/q) is equal to or far larger than 1, which is an ideal value, isomers (which are not necessary for the adsorption of the organometallic complex) may be formed and the formed isomers may degrade the conversion efficiency characteristics of the dye of the solar cell. Accordingly, when the mole ratio of L to Z (p/q) is in the range of about 1 to about 1.4, the isomers (which are not necessary for the adsorption of the organometallic complex) are not formed and thus, the dye-sensitized solar cell including the dye has high current and the photoelectric conversion efficiency thereof is increased.

For example, the dye for dye-sensitized solar cells may include an organometallic complex represented by Formula 6 below, which is formed when, in Formula 1, X is —NCS, L is represented by Formula 4, Z is represented by Formula 5, the mole ratio of L to Z (p/q) is 1, and the amount of the organometallic complex is in the range of 70 to 99 weight (wt) % based on the total weight of the dye:

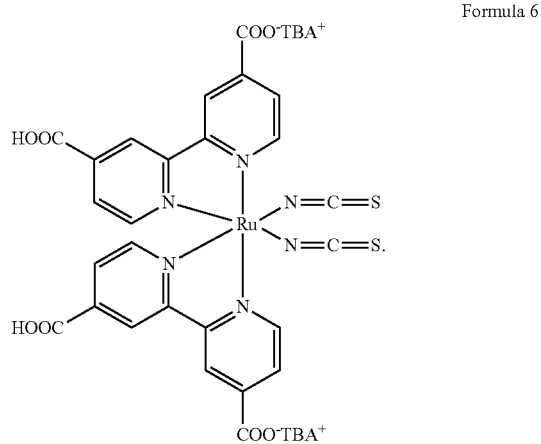

Formula 6

The dye for dye-sensitized solar cells may further include an organometallic complex in which the ratio of L to Z (p/q) is not 1:1 (for example, L:Z may be 2:1) or an isomer in which X is —S=C=N.

The mole ratio of L to Z (p/q) may be controlled by adjusting the pH of the organometallic complex represented by Formula 1 to be in the range of about 3.8 to about 4.1 during the purification process in the method of preparing the organometallic complex represented by Formula 1.

A method of preparing the dye for dye-sensitized solar cells, according to an embodiment of the present invention, includes preparing an organometallic complex represented by Formula 7 below, mixing 100 parts by weight of the organometallic complex, about 80 to about 150 parts by weight of tetrabutylammonium thiocyanate, and about 20 to about 80 parts by weight of tetrabutylammonium hydroxide to prepare a solution, and purifying the solution at a pH of about 3.8 to about 4.1:

ML$_2$X$_2$:Z$_2$  Formula 7

In Formula 7, M, X, L, and Z are the same as described above.

An example of the method of preparing the dye for dye-sensitized solar cells will now be described.

A mixture including dichloro(p-cymene)ruthenium(II) dimer (0.2 mmol, 1 equivalent) and 4,4'-bis(carboxylic acid)-2,2'-bipyridine (0.8 mmol, 4 equivalents) is stirred in a solvent of dimethylformamide (DMF) at a temperature of 160° C. for 4 hours and then distilled. Then, NH$_4$NCS (4 mmol, 10 equivalents) is added thereto and then the resultant is stirred at a temperature of 130° C. for 5 hours and then distilled. The solvent used is removed by evaporation under vacuum conditions and excess water is added to the resultant product and filtering is performed thereon by using a reduced pressure flask, thereby obtaining a violet solid that is not dissolved in water. The violet solid is washed with water and diethylether. Then, the violet solid is dissolved with an aqueous solution of tetra-butyl ammonium hydroxide (2 equivalents) and the obtained solution is loaded into a Sephadex LH-20 column to isolate impurities. In this regard, water is used as an eluate. A pH of the isolated solution is controlled to be in the range of about 3.8 to about 4.1 by using 0.01 M nitric acid and the pH-controlled solution is re-crystallized at a temperature of 4° C. for 12 hours.

The mole ratio of the bidentate ligand to the counter-ion may change according to the pH in the purification process. When the pH is in the range of about 3.8 to about 4.1, the mole ratio of the bidentate ligand to the counter-ion is greater than 1, an ideal ratio. If the pH is outside the range described above, isomers may be formed and the solar cell including the dye may have low conversion efficiency. Examples of such isomers include those represented by Formulae 8 and 9 below.

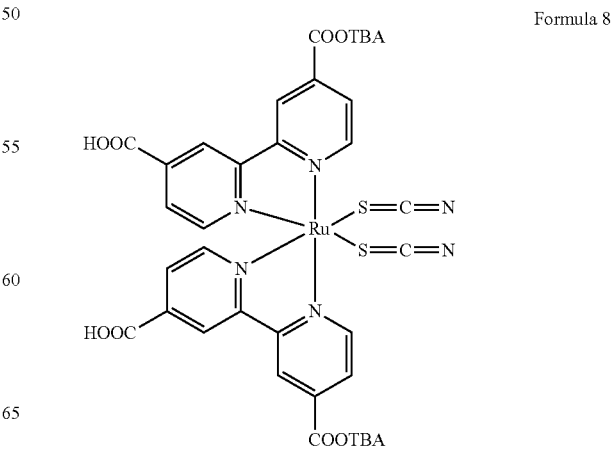

Formula 8

-continued

Formula 9

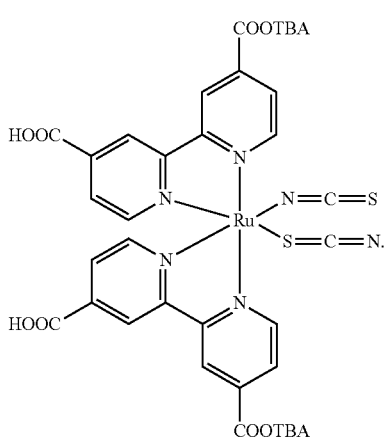

A dye for dye-sensitized solar cells prepared using the method described above may include the organometallic complex represented by Formula 6 in an amount of about 70 to about 99 wt %.

Formula 6

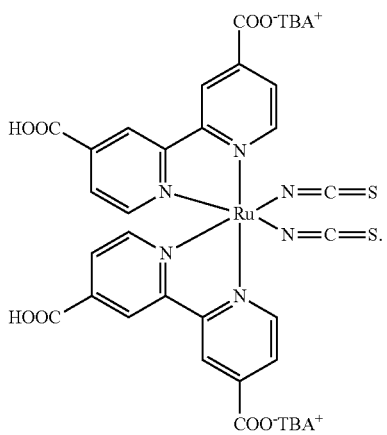

The compound of Formula 6 is formed when, in Formula 1, M is Ru, X is NCS, L is 2,2'-bipyridyl-4,4'-dicarboxylic acid, and Z is tetrabutylammonium.

The unsubstituted $C_{1-20}$ alkyl group may be a linear or branched group, and nonlimiting examples thereof include methyl, ethyl, propyl, isobutyl, sec-butyl, pentyl, iso-amyl, hexyl, heptyl, octyl, nonyl, decyl, undecyl, and dodecyl. In the unsubstituted $C_{1-20}$ alkyl group, at least one hydrogen atom may be substituted with a substituent selected from heavy hydrogen atoms, halogen atoms, cyano groups, amino groups, amidino groups, nitro groups, hydroxyl groups, hydrazinyl groups, hydrazonyl groups, carboxyl groups or salts thereof, sulfonic acid groups or salts thereof, phosphoric acid groups or salts thereof, $C_{1-10}$ alkyl groups, $C_{1-10}$ alkoxy groups, $C_{2-10}$ alkenyl groups, $C_{2-10}$ alkynyl groups, $C_{6-10}$ aryl groups, and $C_{4-10}$ heteroaryl groups.

The unsubstituted $C_{1-20}$ alkoxy group may be a group represented by —OA where A is an unsubstituted $C_{1-20}$ alkyl group (which is as described above). Nonlimiting examples of the unsubstituted $C_{1-20}$ alkoxy group include methoxy groups, ethoxy groups, propoxy groups, isopropyloxy groups, butoxy groups, and pentoxy groups. In the unsubstituted $C_{1-20}$ alkoxy group, at least one hydrogen atom may be substituted with a substituent selected from those described above in connection with the $C_{1-20}$ alkyl group.

The unsubstituted $C_{2-20}$ alkenyl group contains at least one carbon-carbon double bond at the middle or end of the unsubstituted $C_{2-20}$ alkyl group described above. Examples of the unsubstituted $C_{2-20}$ alkenyl group include ethenyl, propenyl, and butenyl. However, an example of the unsubstituted $C_{2-20}$ alkenyl group is not limited thereto. In the unsubstituted $C_{2-20}$ alkenyl group, at least one hydrogen atom may be substituted with the same substituent as described above in connection with the $C_{1-20}$ alkyl group.

The unsubstituted $C_{2-20}$ alkynyl group contains at least one carbon triple bond at the middle or end of an unsubstituted $C_{2-20}$ alkyl group (which is as described above). Nonlimiting examples of the unsubstituted $C_{2-20}$ alkynyl group include acetylene groups, propylene groups, phenylacetylene groups, naphthylacetylene groups, isopropylacetylene groups, t-butylacetylene groups, and diphenylacetylene groups. In the alkynyl group, at least one hydrogen atom may be substituted with a substituent selected from those described above in connection with the $C_{1-20}$ alkyl group.

The unsubstituted $C_{6-30}$ aryl group is a carbocyclic aromatic system containing at least one ring, and when the carbocyclic aromatic system has two or more rings, the rings may be fused together or connected to each other by a single bond. The term 'aryl' includes an aromatic system such as phenyl, naphthyl, or anthracenyl. In addition, in the unsubstituted $C_{6-30}$ aryl group, at least one hydrogen atom may be substituted with a substituent selected from those described above in connection with the $C_{1-20}$ alkyl group. Nonlimiting examples of the unsubstituted $C_{6-30}$ aryl group include phenyl groups, $C_{1-10}$ alkylphenyl groups (for example, ethylphenyl groups), halophenyl groups (for example, o-, m- and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_{1-10}$ alkylbiphenyl groups, $C_{1-10}$ alkoxy biphenyl groups, o-, m- and p-tolyl groups, o-, m- and p-cumenyl groups, mesityl groups, phenoxyphenyl groups, (α,α-dimethylbenzene) phenyl groups, (N,N"-dimethyl)aminophenyl groups, (N,N'-diphenyl)amino phenyl groups, pentalenyl groups, indenyl groups, naphthyl groups, halonaphthyl groups (for example, fluoronaphthyl groups), $C_{1-10}$ alkylnaphthyl groups (for example, methylnaphthyl groups), $C_{1-10}$ alkoxy naphthyl groups (for example, methoxynaphthyl groups), cyanonaphthyl groups, anthracenyl groups, azulenyl groups, a heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, phenylenyl groups, chlorophenylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_{6-30}$ aryloxy group is a group represented by —OA1 where A1 is a $C_{6-30}$ aryl group. Nonlimiting examples of the unsubstituted $C_{6-30}$ aryloxy group include phenoxy groups. In the unsubstituted $C_{6-30}$ aryloxy group, at least one hydrogen atom may be substituted with a substituent selected from those described above in connection with the $C_{1-20}$ alkyl group.

The unsubstituted $C_{2-30}$ heteroaryl group includes one, two, or three hetero atoms selected from N, O, P, and S, and when the unsubstituted $C_{2-30}$ heteroaryl group has two or more rings, the rings may be fused together or connected to each other by a single bond. Nonlimiting examples of the unsubstituted $C_{2-30}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In the unsubstituted $C_{2-30}$ heteroaryl group, at least one hydrogen atom may be substituted with a substituent selected from those described above in connection with the $C_{1-20}$ alkyl group.

A dye-sensitized solar cell according to an embodiment of the present invention includes a first electrode including a conductive transparent substrate; a light absorbing layer formed on a surface of the first electrode; a second electrode disposed facing the surface of the first electrode on which the light absorbing layer is formed; and an electrolyte between the first electrode and the second electrode. The light absorbing layer includes micro-semiconducting particles and a dye for use in dye-sensitized solar cells, and includes the organometallic complex represented by Formula 1.

The organometallic complex represented by Formula 1 is useful as a dye molecule in a dye-sensitized solar cell. The dye-sensitized solar cell includes a first electrode, a light absorbing layer, a second electrode, and an electrolyte, and the light absorbing layer may include micro-semiconducting particles and dye molecules. The organometallic complex represented by Formula 1 may be used as the dye molecule of the light absorbing layer.

Figure 2:
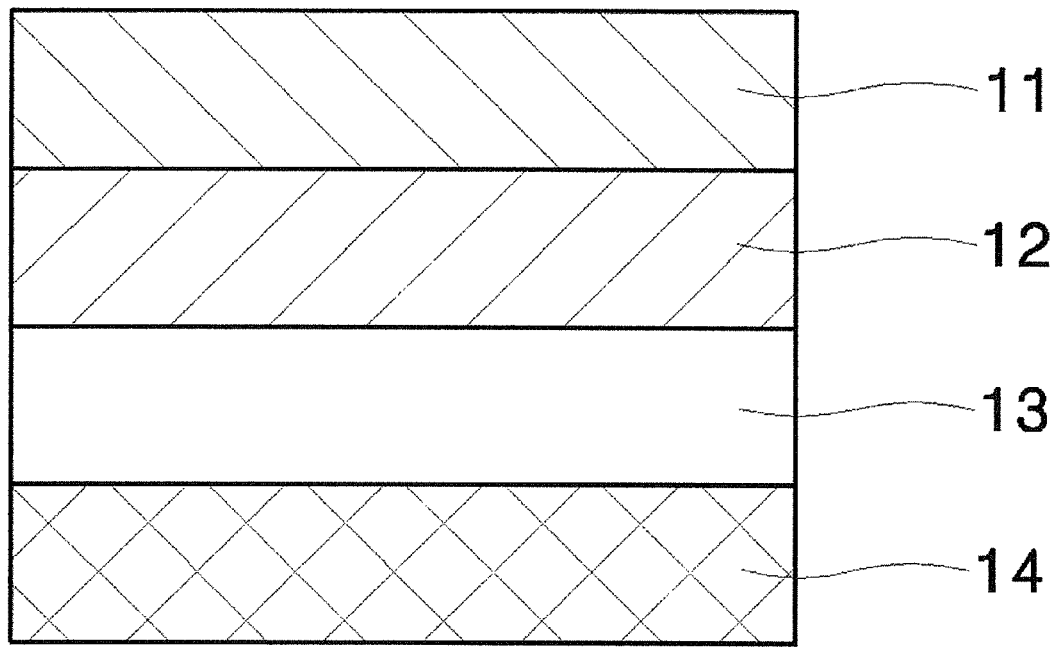
FIG. 2 is a cross-sectional view of a dye-sensitized solar cell according to an embodiment of the present invention.
Figure 3A:
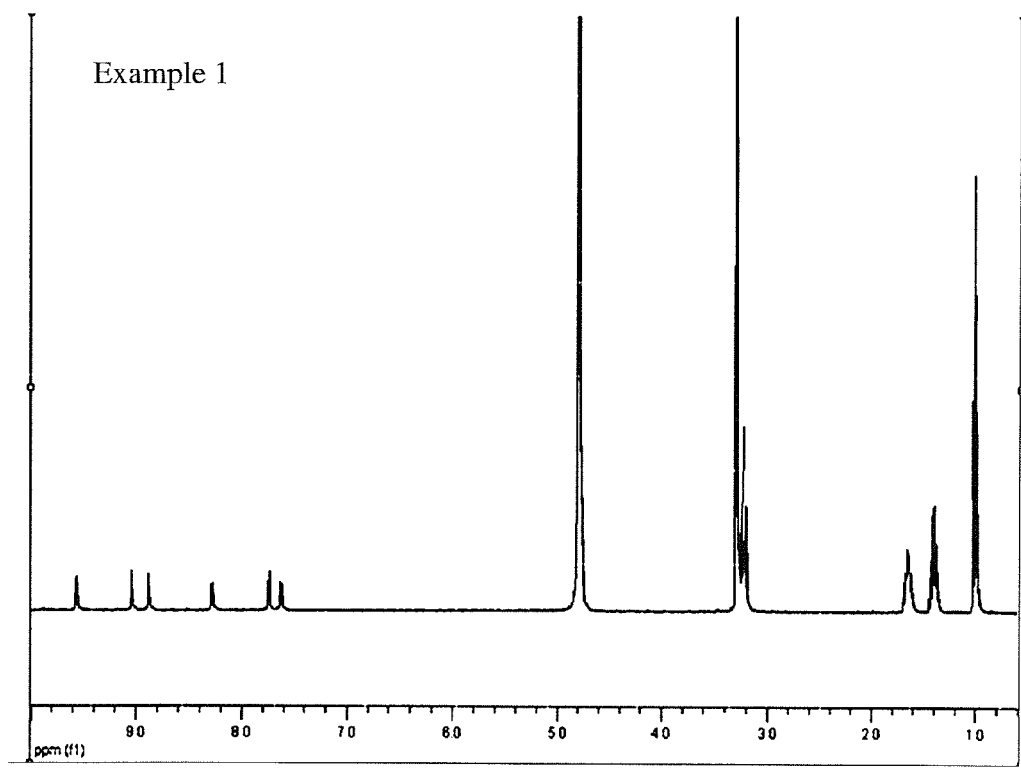
FIGS. 3A through 3F are nuclear magnetic resonance (NMR) spectra of dye—the sensitized solar cells manufactured according to Examples 1-2 and Comparative Examples 1-4, respectively.
Figure 3B:
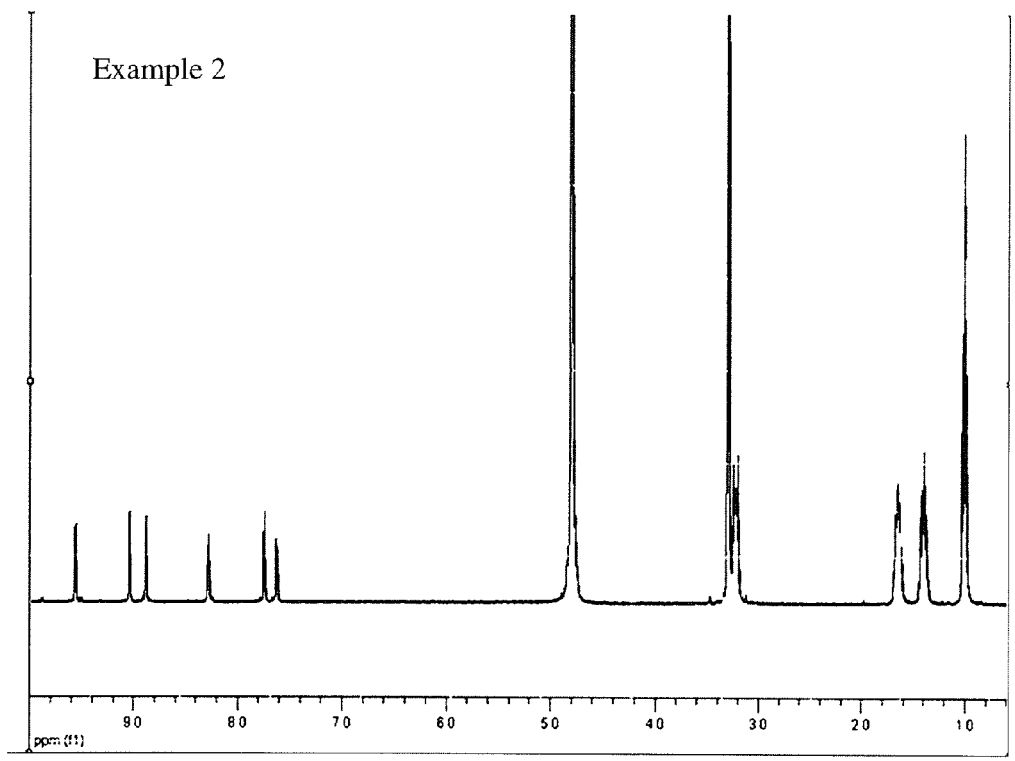
Figure 3C:
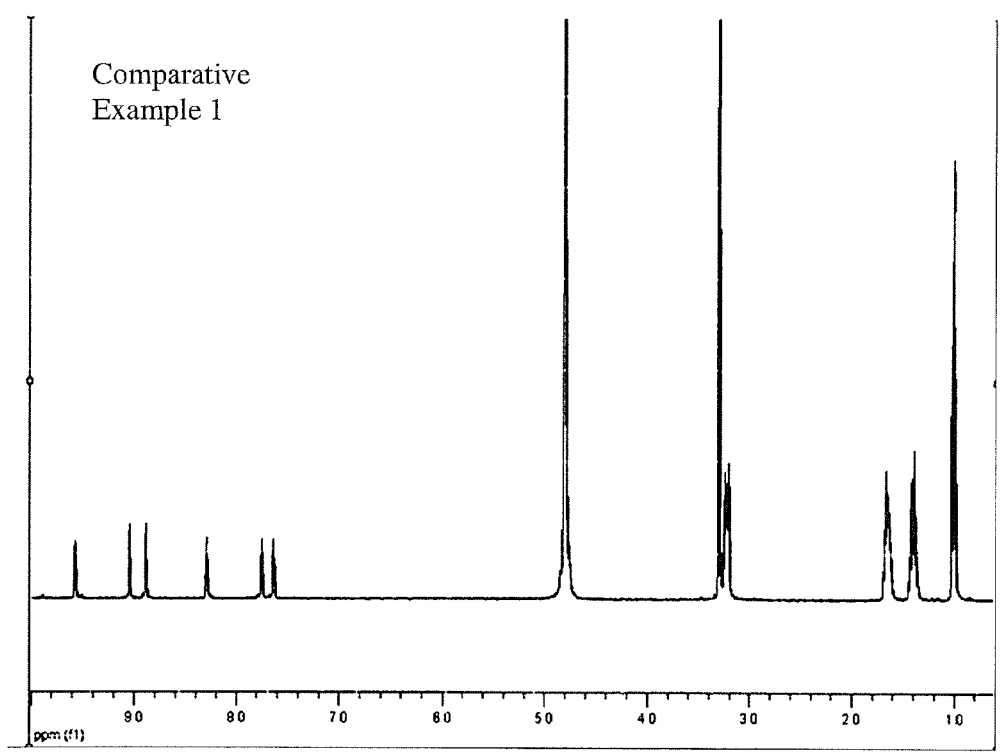
Figure 3D:
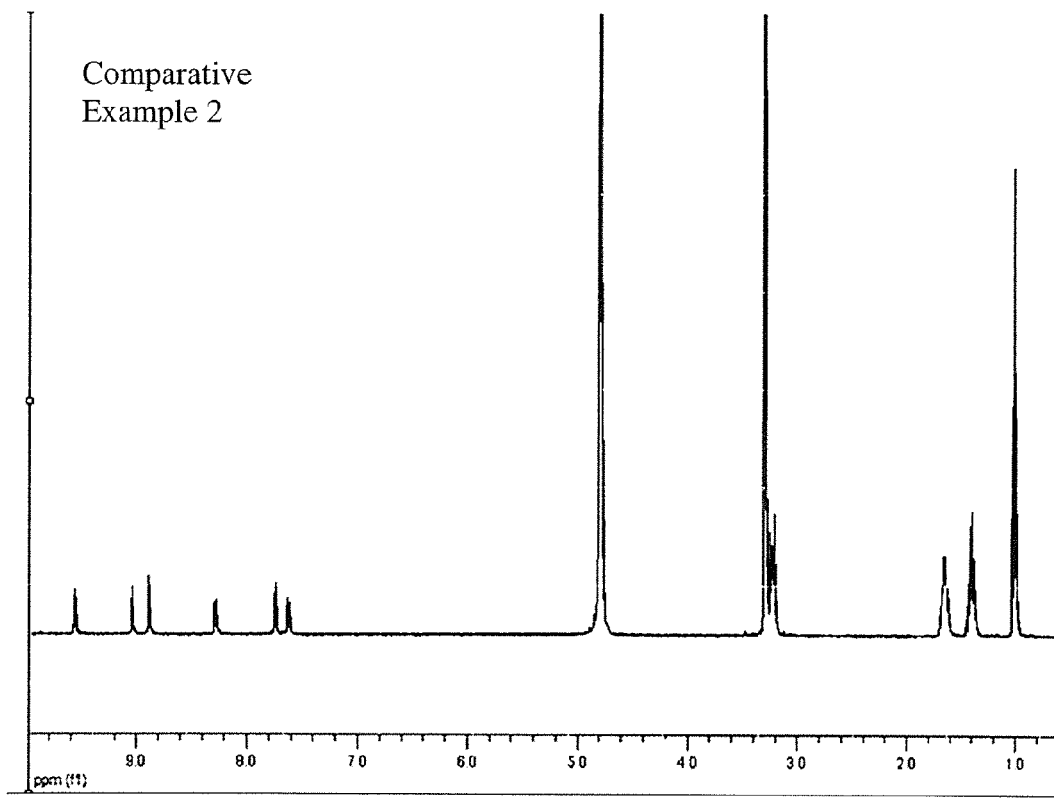
Figure 3E:
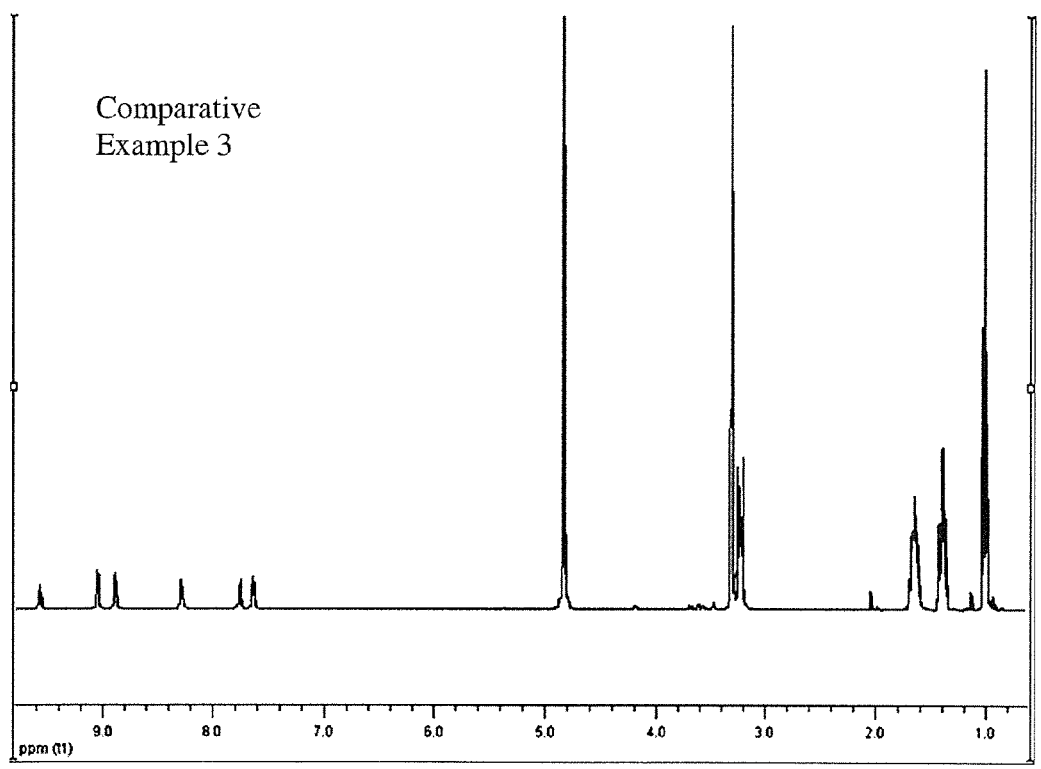
Figure 3F:
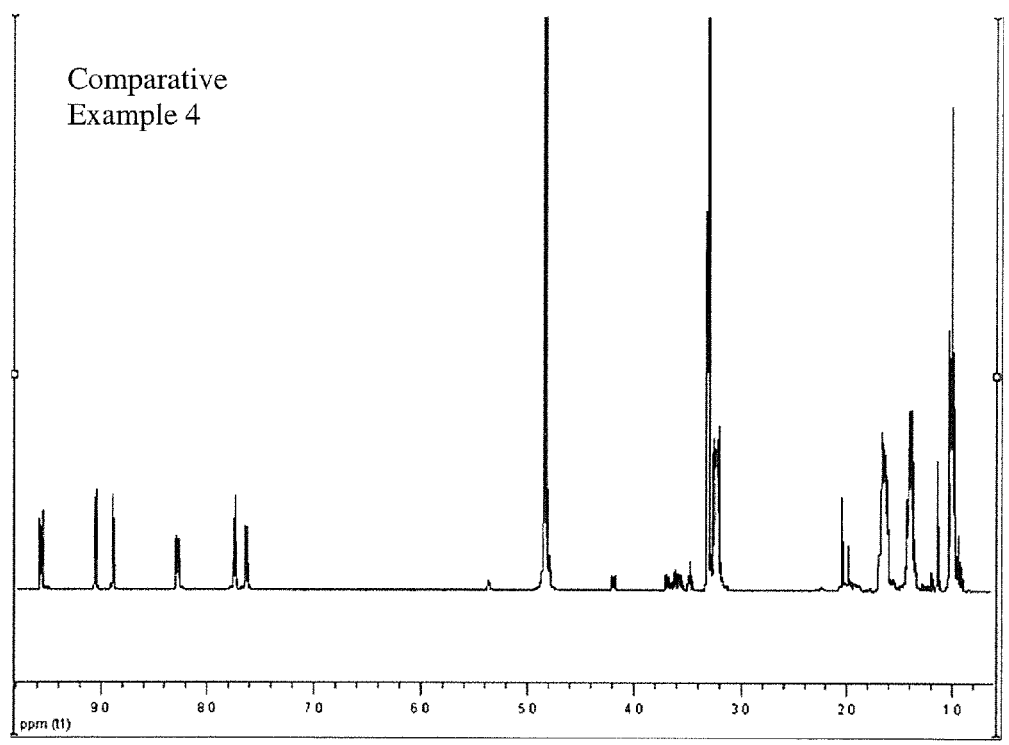

FIG. 2 is a cross-sectional view of a dye-sensitized solar cell according to an embodiment of the present invention. The dye-sensitized solar cell includes a first electrode 11, a light absorbing layer 12, an electrolyte 13, and a second electrode 14. The light absorbing layer 12 may include micro-semiconducting particles and dye molecules. As described above, the organometallic complex represented by Formula 1 may be used as the dye molecules of the light absorbing layer 12. Meanwhile, the first electrode 11 and the light absorbing layer 12 may constitute a semiconductor electrode.

The first electrode 11 may be a transparent substrate, and the transparent substrate may be any of various transparent substrates. For example, the transparent substrate may be a glass substrate. In addition, a material for providing conductivity to the transparent substrate may be any of various materials that have conductivity and transparency. For example, the material may be a tin-based oxide (for example, $SnO_2$) with conductivity, transparency, and high resistance to heat, or an indium tin oxide (ITO) which is relatively inexpensive.

The light absorbing layer 12 may include micro-semiconducting particles and dye molecules, and a thickness of the light absorbing layer 12 may be equal to or smaller than 15 µm. In some embodiments, for example, the thickness of the light absorbing layer may be in the range of about 1 to about 15 µm. Due to its structure, the light absorbing layer 12 has a high series resistance, and such a high series resistance leads to a decrease in conversion efficiency. Thus, by controlling the thickness of the light absorbing layer 12 to be equal to or smaller than 15 µm, the series resistance of the light absorbing layer 12 may be maintained at lower levels while the functions of the light absorbing layer 12 are maintained, and thus, decreases in conversion efficiency may be substantially prevented.

The micro-semiconducting particles of the light absorbing layer 12 may be selected from semiconductor materials including silicon, compound semiconductors, and compounds having a Perovskite structure. These semiconductors may be n-type semiconductors in which, when excited by light, conduction band electrons act as a carrier and provide a negative current. For example, the micro-semiconducting particles may be titanium dioxide ($TiO_2$), $SnO_2$, ZnO, $WO_3$, $Nb_2O_5$, or $TiSrO_3$. For example, the micro-semiconducting particles may be Anatase-type $TiO_2$. However, the micro semiconducting particles are not limited thereto, and these semiconductors may be used alone or in combination. The micro-semiconducting particles may contribute a large surface area so that the dye adsorbed to the surfaces of the micro-semiconducting particles absorbs more light. To do this, the diameters of the micro-semiconducting particles may be equal to or smaller than 20 nm.

The dye of the light absorbing layer includes the organometallic complex represented by Formula 1. A description of the organometallic complex represented by Formula 1 has been presented above.

A method of manufacturing the light absorbing layer 12 will now be described. A solution in which the organometallic complex represented by Formula 1 is dispersed in a solvent is sprayed or coated on the surfaces of the micro-semiconducting particles, or the micro-semiconducting particles are immersed in the solution. Then, the micro-semiconducting particles are washed and dried to manufacture the light absorbing layer 12. Alternatively, the micro-semiconducting particles are formed on the first electrode 11, and then the solution in which the organometallic complex represented by Formula 1 is dispersed in a solvent is sprayed or coated on the surfaces of the micro-semiconducting particles, thereby completing the manufacture of the light absorbing layer 12. The solvent for dispersing the organometallic complex is not limited and may be an acetonitrile solvent, a dichloromethane solvent, or an alcohol-based solvent.

In the method described above, after the organometallic complex represented by Formula 1 is formed on the micro-semiconducting particles, the resultant may be washed with a solvent to form a single layer.

The electrolyte 13 may include an electrolytic solution including an $I^-/I^{3-}$ oxidation-reduction pair. The electrolytic solution may be, for example, an acetonitrile solution of iodine, but is not limited thereto. The electrolytic solution may be any of various electrolytic solutions that conduct holes.

The second electrode 14 may be formed of a conductive material. The conductive material for forming the second electrode 14 may be any of various conductive materials. In addition, if a conductive layer is disposed facing the semiconductor electrode, an insulating material may also be used to form the second electrode 14. The conductive material and the insulating material for forming the second electrode 14 should be electrochemically stable. For example, the second electrode 14 may be formed of platinum, gold, or carbon. In addition, in order to improve the catalytic effect for oxidation and reduction, a surface of the second electrode 14 facing the semiconductor electrode may have a micro-structure and a large surface area. For example, the second electrode 14 may be formed of platinum black or a porous carbon. The platinum black may be formed by an anodizing process performed on platinum or a treatment using chloroplatinic acid. The porous carbon may be formed by sintering carbon microparticles or calcining an organic polymer.

The following examples are presented for illustrative purposes only and do not limit the scope of the invention.

Example 1

Purification of $Ru(dcbpvH)_2(NCS)_2(TBA)_2$

As used herein, dcbpyH represents 2,2'-bipyridyl-4,4'-dicarboxylic acid, and TBA represents tetrabutylammonium.

0.50 g of $Ru(dcbpyH)_2(NCS)_2(TBA)_2$, 0.58 g of tetrabutylammonium thiocyanate, and 0.27 g of tetrabutylammonium hydroxide were completely dissolved with 100 ml of triple distilled water. The mixed solution was loaded into a column filled with Sepadex LH-20 while being poured together with distilled water. Only a dark band formed at the middle of the column was isolated, and a pH of the isolated solution was adjusted to be 3.8 using an aqueous nitric acid solution. The solution with a pH of 3.8 was frozen at a temperature of −7° C. for one day, and then the frozen product was melted and filtered through filter paper. The filtered product was vacuum-dried, thereby preparing a dye.

A mole ratio of dcbpyH to TBA and the amount of the organometallic complex represented by Formula 6 were evaluated using 1H-NMR.

Manufacturing of a Dye-Sensitized Solar Cell

A dispersion of titanium oxide particles was coated on a fluorine-doped tin oxide transparent conductive substrate using a doctor blade. The diameters of the titanium oxide particles used were in the range of about 15 to about 20 nm and the coated area was 0.18 cm². The resultant was calcined at a temperature of 500° C. for 30 minutes, thereby forming a porous titanium oxide layer having a thickness of 15 μm. The porous titanium oxide layer was subjected to an adsorption process using 0.2 mM of a dye solution prepared by dissolving the dye in ethanol for at least 18 hours. Then, the dye-adsorbed porous titanium oxide layer was washed with ethanol and dried, thereby manufacturing a semiconductor electrode.

As an opposite electrode, a Pt layer was formed on a fluorine-doped tin oxide transparent conductive substrate by sputtering. The opposite electrode had micro-pores for injection of an electrolytic solution. The micro-pores were formed using a drill having a diameter of 0.6 mm.

A thermoplastic polymer film having a thickness of 60 μm was positioned between the semiconductor electrode and the opposite electrode and the resultant structure was compressed at a temperature of 90° C. for 10 seconds, thereby joining the semiconductor electrode and the opposite electrode. A redox electrolyte was injected into the opposite electrode through the micro-pores formed in the opposite electrode, and then the micro-pores were sealed by a cover glass and a thermoplastic polymer film, thereby completing the manufacture of the dye-sensitized solar cell. The redox electrolyte was prepared by dissolving 0.62 M of 1-butyl-3-methylimidazolium iodide, 0.1 M of LiI, 0.5 M of $I_2$, and 0.5 M of 4-tert-butylpyridine in acetonitrile.

A xenon lamp (Oriel, 01193) was used as a light source, and a solar condition (AM 1.5) of the xenon lamp was corrected using a standard solar cell (Frunhofer Institute Solare Engeriessysteme, a Certificate No. C-ISE369, Type of material: Mono-Si+KG filter). In a measured photocurrent and voltage graph, the voltage ($V_{oc}$) was 0.751 V, the current density ($J_{sc}$) was 18.745 mA/cm², the fill factor (FF) was 68.2, and the photo conversion efficiency (Eff) measured using Equation 1 below was 9.60%.

$$Eff=(V_{oc}J_{sc}FF)/(P_{inc})$$ Equation 1

In Equation 1, $P_{inc}$ is 100 mW/cm² (1 sun).

Example 2

Purification of Ru(dcbpyH)$_2$NCS TBA)$_2$ 0.50 g of Ru(dcbpyH)$_2$(NCS)$_2$(TBA)$_2$, 0.58 g of tetrabutylammonium thiocyanate, and 0.27 g of tetrabutylammonium hydroxide were completely dissolved with 100 ml of triple distilled water. The mixed solution was loaded into a column filled with Sepadex LH-20 while being poured together with distilled water. Only a dark band formed at the middle of the column was isolated, and a pH of the isolated solution was adjusted to 4.0 using an aqueous nitric acid solution. The solution with the pH of 4.0 was frozen at a temperature of −7° C. for one day, and then the frozen product was melted and filtered through filter paper. The filtered product was vacuum-dried, thereby preparing a dye.

A mole ratio of dcbpyH to TBA and the amount of the organometallic complex represented by Formula 6 were evaluated using 1H-NMR.

Manufacture of Dye-Sensitized Solar Cell

A dye-sensitized solar cell was manufactured as in Example 1, except that the dye obtained by purification at a pH of 4.0 was used.

In a measured photocurrent and voltage graph, the voltage ($V_{oc}$) was 0.738 V, the current density ($J_{sc}$) was 19.547 mA/cm², the fill factor (FF) was 69.0, and the photo conversion efficiency (Eff) measured using Equation 1 above was 9.95%.

Comparative Example 1

Purification of Ru(dcbpyH)$_2$(NCS)$_2$(TBA)$_2$ 0.5 g of Ru(dcbpyH)$_2$(NCS)$_2$(TBA)$_2$, 0.58 g of tetrabutylammonium thiocyanate, and 0.27 g of tetrabutylammonium hydroxide were completely dissolved with 100 ml of triple distilled water. The mixed solution was loaded into a column filled with Sepadex LH-20 while being poured together with distilled water. Only a dark band formed at the middle of the column was isolated, and a pH of the isolated solution was adjusted to 3.4 using an aqueous nitric acid solution. The solution with the pH of 3.4 was frozen at a temperature of −7° C. for one day, and then the frozen product was melted and filtered through filter paper. The filtered product was vacuum-dried, thereby preparing a dye.

A mole ratio of dcbpyH to TBA and the amount of the organometallic complex represented by Formula 6 were evaluated using 1H-NMR.

Manufacture of Dye-Sensitized Solar Cell

A dye-sensitized solar cell was manufactured as in Example 1, except that the dye obtained by purification at a pH of 3.4 was used.

In a measured photocurrent and voltage graph, the voltage ($V_{oc}$) was 0.733 V, the current density ($J_{sc}$) was 18.809 mA/cm², the fill factor (FF) was 68.3, and the photo conversion efficiency (Eff) measured using Equation 1 above was 9.42%.

Comparative Example 2

Purification of Ru(dcbpyH)$_2$(NCS)$_2$(TBA)$_2$ 0.5 g of Ru(dcbpyH)$_2$(NCS)$_2$(TBA)$_2$, 0.58 g of tetrabutylammonium thiocyanate and 0.27 g of tetrabutylammonium hydroxide were completely dissolved with 100 ml of triple distilled water. The mixed solution was loaded into a column filled with Sepadex LH-20 while being poured together with distilled water. Only a dark band formed at the middle of the column was isolated, and a pH of the isolated solution was adjusted to 3.6 using an aqueous nitric acid solution. The solution with the pH of 3.6 was frozen at a temperature of −7° C. for one day, and then the frozen product was melted and filtered through filter paper. The filtered product was vacuum-dried, thereby preparing a dye.

A mole ratio of dcbpyH to TBA and the amount of the organometallic complex represented by Formula 6 were evaluated using 1H-NMR.

Manufacture of Dye-sensitized Solar Cell

A dye-sensitized solar cell was manufactured as in Example 1, except that the dye obtained by purification at a pH of 3.6 was used.

In a measured photocurrent and voltage graph, the voltage ($V_{oc}$) was 0.730 V, the current density ($J_{sc}$) was 16.043 mA/cm$^2$, the fill factor (FF) was 68.7, and the photo conversion efficiency (Eff) measured using Equation 1 above was 8.05%.

Comparative Example 3

Purification of Ru(dcbpyH)$_2$(NCS)$_2$(TBA)$_2$ 0.5 g of Ru(dcbpyH)$_2$(NCS)$_2$(TBA)$_2$, 0.58 g of tetrabutylammonium thiocyanate, and 0.27 g of tetrabutylammonium hydroxide were completely dissolved with 100 ml of triple distilled water. The mixed solution was loaded into a column filled with Sepadex LH-20 while being poured together with distilled water. Only a dark band formed at the middle of the column was isolated and a pH of the isolated solution was adjusted to 4.2 using an aqueous nitric acid solution. The solution with the pH of 4.2 was frozen at a temperature of −7° C. for one day, and then the frozen product was melted and filtered through filter paper. The filtered product was vacuum-dried, thereby preparing a dye.

A mole ratio of dcbpyH to TBA and the amount of the organometallic complex represented by Formula 6 were evaluated using 1H-NMR.

Manufacture of Dye-Sensitized Solar Cell

A dye-sensitized solar cell was manufactured as in Example 1, except that the dye obtained by purification at a pH of 4.2 was used.

In a measured photocurrent and voltage graph, the voltage ($V_{oc}$) was 0.723 V, the current density ($J_{sc}$) was 18.887 mA/cm$^2$, the fill factor (FF) was 68.8, and the photo conversion efficiency (Eff) measured using Equation 1 above was 9.39%.

Comparative Example 4

Purification of Ru(dcbpyH)$_2$(NCS)$_2$(TBA)$_2$ 0.5 g of Ru(dcbpyH)$_2$(NCS)$_2$(TBA)$_2$, 0.58 g of tetrabutylammonium thiocyanate and 0.27 g of tetrabutylammonium hydroxide were completely dissolved with 100 ml of triple distilled water. The mixed solution was loaded into a column filled with Sepadex LH-20 while being poured together with distilled water. Only a dark band formed at the middle of the column was isolated, and a pH of the isolated solution was adjusted to 4.4 using an aqueous nitric acid solution. The solution with the pH of 4.4 was frozen at a temperature of −7° C. for one day, and then the frozen product was melted and filtered through filter paper. The filtered product was vacuum-dried, thereby preparing a dye.

A mole ratio of dcbpyH to TBA and the amount of the organometallic complex represented by Formula 6 were evaluated using 1H-NMR.

Manufacture of Dye-Sensitized Solar Cell

A dye-sensitized solar cell was manufactured as in Example 1, except that the dye obtained by purification at a pH of 4.4 was used.

In a measured photocurrent and voltage graph, the voltage ($V_{oc}$) was 0.714 V, the current density ($J_{sc}$) was 18.324 mA/cm$^2$, the fill factor (FF) was 68.5, and the photo conversion efficiency (Eff) measured using Equation 1 above was 8.96%.

The pH during purification and the mole ratio of dcbpyH to TBA of the dyes prepared according to Examples 1-2 and Comparative Examples 1-4 are shown in Table 1 below. Nuclear magnetic resonance (NMR) data for the evaluation of the mole ratios of dcbpyH to TBA are shown in FIGS. 3A through 3F.

TABLE 1

|  | PH during purification | Mole ratio of dcbpyH to TBA |
| --- | --- | --- |
| Example 1 | 3.8 | 1.38 |
| Example 2 | 4.0 | 1.24 |
| Comparative Example 1 | 3.4 | 1.33 |
| Comparative Example 2 | 3.6 | 1.33 |
| Comparative Example 3 | 4.2 | 1.02 |
| Comparative Example 4 | 4.4 | 0.97 |

The voltages ($V_{oc}$), current densities ($J_{sc}$), fill factors (FF), and photo conversion efficiencies (Eff) of the dye-sensitized solar cells manufactured according to Examples 1-2 and Comparative Examples 1-4 are shown in Table 2 below.

TABLE 2

|  | Voltage ($V_{oc}$) | Current density ($JI_{sc}$) | Fill factor (FF) | Photo conversion efficiency (Eff) |
| --- | --- | --- | --- | --- |
| Example 1 | 0.751 | 18.745 | 68.2 | 9.60 |
| Example 2 | 0.738 | 19.547 | 69.0 | 9.95 |
| Comparative Example 1 | 0.733 | 18.809 | 68.3 | 9.42 |
| Comparative Example 2 | 0.730 | 16.043 | 68.7 | 8.05 |
| Comparative Example 3 | 0.723 | 18.887 | 68.8 | 9.39 |
| Comparative Example 4 | 0.714 | 18.324 | 68.5. | 8.96 |

Referring to Table 2, the dye-sensitized solar cells manufactured according to Examples 1-2 had higher voltages ($V_{oc}$), higher current densities ($J_{sc}$), and higher photo conversion efficiencies (Eff) than the dye-sensitized solar cells manufactured according to Comparative Examples 1-4, although the dye-sensitized solar cells manufactured according to Examples 1-2 and Comparative Examples 1-4 all have similar fill factors (FF).

As described above, a solar cell including a dye for a dye-sensitized solar cell according to embodiments of the present invention has high conversion efficiency.

While certain exemplary embodiments have been described, those of ordinary skill in the art will understand that certain modifications and changes to the described embodiments may be made without departing from the spirit and scope of the disclosure, as described in the appended claims. Moreover, descriptions of features or aspects within each described embodiment should typically be considered as available for other similar features or aspects in other embodiments.

What is claimed is:

1. A dye for a dye-sensitized solar cell, the dye comprising an organometallic complex represented by Formula 1:

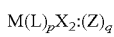    Formula 1 wherein,

M is an element selected from the group consisting of Group 8 through Group 10 metallic elements, X is a co-ligand selected from the group consisting of —CN, —OH, —I, —Cl, —NCO, —NCS, and —NCSe, L is a bidentate ligand represented by Formula 2:

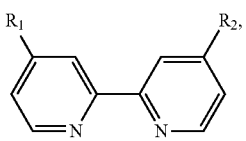    Formula 2

Z is a counter-ion represented by Formula 3:

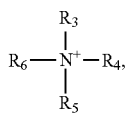    Formula 3 and p equals 2, and the mole ratio of p to q is about 1.1 to about 1.4, wherein:

each of $R_1$ and $R_2$ is independently selected from the group consisting of COOH, $PO_3H_2$, $PO_4H_2$, $SO_3H_2$, $SO_4H_2$, and CONHOH, at least one of $R_1$ and $R_2$ is deprotonized, and each of $R_3$ through $R_6$ is independently selected from the group consisting of substituted and unsubstituted $C_{1-20}$ alkyl groups, substituted and unsubstituted $C_{1-20}$ alkoxy groups, substituted and unsubstituted $C_{2-20}$ alkenyl groups, substituted and unsubstituted $C_{2-20}$ alkynyl groups, substituted and unsubstituted $C_{6-30}$ aryl groups, substituted and unsubstituted $C_{6-30}$ aryloxy groups, and substituted and unsubstituted $C_{2-30}$ heteroaryl groups.

2. The dye of claim 1, wherein M is ruthenium (Ru).

3. The dye of claim 1, wherein X is —NCS.

4. The dye of claim 1, wherein L is represented by Formula 4:

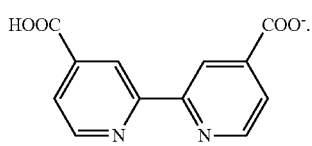    Formula 4

5. The dye of claim 1, wherein Z is represented by Formula 5:

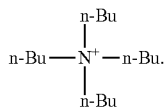    Formula 5

6. The dye of claim 1, wherein M is Ru, X is —NCS, and L is a bidentate ligand represented by Formula 2:

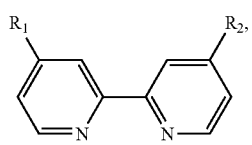    Formula 2 wherein each of $R_1$ and $R_2$ is independently selected from the group consisting of COOH, $PO_3H_2$, $PO_4H_2$, $SO_3H_2$, $SO_4H_2$, and CONHOH, and at least one of $R_1$ and $R_2$ is deprotonized.

7. The dye of claim 1, wherein M is Ru, X is —NCS, and Z is represented by Formula 5:

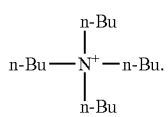    <Formula 5>

8. The dye of claim 1, wherein the dye comprises about 70 to about 99 wt % of an organometallic complex represented by Formula 6:

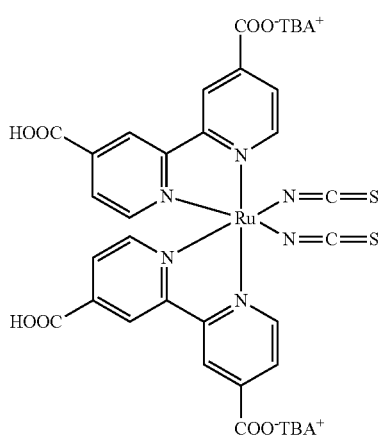    Formula 6

9. A method of preparing the dye of claim 1, the method comprising:

preparing an organometallic complex represented by Formula 7, mixing 100 parts by weight of the organometallic complex, about 80 to about 150 parts by weight of tetrabutylammonium thiocyanate, and about 20 to about 80 parts by weight of tetrabutylammonium hydroxide to prepare a solution, and purifying the solution at a pH of about 3.8 to about 4.1:

$$ML_2X_2 \cdot Z_2 \qquad \text{Formula 7}$$

wherein:
M is an element selected from the group consisting of Group 8 through Group 10 metallic elements,
X is a co-ligand selected from the group consisting of —CN, —OH, —I, —Cl, —NCO, —NCS, and —NCSe,
L is a bidentate ligand represented by Formula 2:

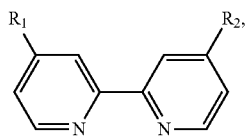

Formula 2

Z is a counter-ion represented by Formula 3:

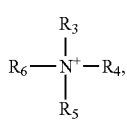

Formula 3 wherein:
each of $R_1$ and $R_2$ is independently selected from the group consisting of COOH, $PO_3H_2$, $PO_4H_2$, $SO_3H_2$, $SO_4H_2$, and CONHOH, and at least one of $R_1$ and $R_2$ is deprotonized, and
each of $R_3$ through $R_6$ is independently selected from the group consisting of substituted and unsubstituted $C_{1-20}$ alkyl groups, substituted and unsubstituted $C_{1-20}$ alkoxy groups, substituted and unsubstituted $C_{2-20}$ alkenyl groups, substituted and unsubstituted $C_{2-20}$ alkynyl groups, substituted and unsubstituted $C_{6-30}$ aryl groups, substituted and unsubstituted $C_{6-30}$ aryloxy groups, and substituted and unsubstituted $C_{2-30}$ heteroaryl groups.

10. The method of claim 9, wherein M is Ru.
11. The method of claim 9, wherein X is —NCS.
12. The method of claim 9, wherein L is represented by Formula 4 below:

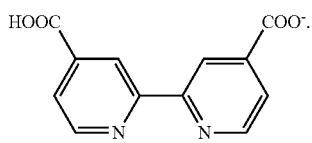

Formula 4

13. The method of claim 9, wherein Z is represented by Formula 5:

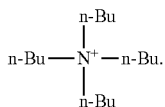

Formula 5

14. The method of claim 9, wherein the dye comprises about 70 to about 99 wt % of an organometallic complex represented by Formula 6:

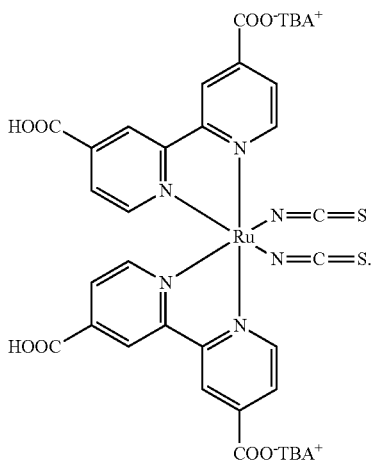

Formula 6

15. A dye-sensitized solar cell comprising:
a first electrode comprising a conductive transparent substrate;
a light absorbing layer on a surface of the first electrode;
a second electrode facing the light absorbing layer on the surface of the first electrode; and
an electrolyte between the first electrode and the second electrode,
wherein the light absorbing layer comprises micro-semiconducting particles and the dye of claim 1.

16. The dye-sensitized solar cell of claim 15, wherein the light absorbing layer has a thickness of about 1 to about 15 μm.

* * * * *